US00PP17767P3

(12) United States Plant Patent
Zengji et al.

(10) Patent No.: US PP17,767 P3
(45) Date of Patent: May 29, 2007

(54) ×*TAXODIOMERIA PEIZHONGII* TREE NAMED 'DONGFANGSHAN'

(50) Latin Name: ×*Taxodiomera peizhongii*
Varietal Denomination: Dongfangshan

(75) Inventors: Ye Zengji, Shanghai (CN); Shen Lieying, Shanghai (CN); Pan Shihua, Shanghai (CN); Zhu Weijie, Shanghai (CN); Niu Huijuan, Shanghai (CN)

(73) Assignee: Shanghai Forestry Station, Shanghai (CN)

( * ) Notice: Subject to any disclaimer, the term of this patent is extended or adjusted under 35 U.S.C. 154(b) by 0 days.

(21) Appl. No.: 10/941,465

(22) Filed: Sep. 15, 2004

(65) Prior Publication Data

US 2006/0059593 P1 Mar. 16, 2006

(51) Int. Cl.
*A01H 7/00* (2006.01)

(52) U.S. Cl. ..... Plt./213
(58) Field of Classification Search ..... Plt./213
See application file for complete search history.

(56) References Cited

PUBLICATIONS

Zhang et al. The characteristics and ecological value of *Taxodium mucronatum*×*Cryptomeria,* Jul. 2003. Acta Agriculturae Shanghai, vol. 19, No. 3, pp. 56–59.*

* cited by examiner

*Primary Examiner*—Kent Bell
*Assistant Examiner*—June Hwu
(74) *Attorney, Agent, or Firm*—Armstrong Teasdale LLP

(57) ABSTRACT

×*Taxodiomeria peizhongii* is a distinct and new above ground nontubular propagated cultivar comprising a tall semi-indeciduous arbor tree providing a high view. ×*Taxodiomeria peizhongii* is well suited for afforestation in the city and has many good properties such as fast growth, wide adaptability and strong stress resistance. Its main characteristics include: (1) its base of stem is round and regular without buttress roots; (2) its bark cracks into flakes; (3) there are several main crotches five to eight meters above ground, and its canopy is nearly elliptic shape; (4) there are only male conglobate flower and no female conglobate fruit on the adult tree, and it cannot reproduce with sexual propagation manner. It possesses additional good properties including enhanced saline tolerance (salt content is below about 3.9%), alkali tolerance (7≦pH≦8.9), moisture resistance and good (pleasing visual) landscape effect.

14 Drawing Sheets

Lain name: ×*Taxodiomeria peizhongii.*
Variety denomination: Dongfangshan.

BACKGROUND OF THE NEW CULTIVAR

Field of the Invention

The new cultivar, ×*Taxodiomeria peizhongii,* is the filial generation of *Taxodium mucronatum* Ten and *Cryptomeria fortunei.* The cultivar name of ×*Taxodiomeria peizhongii* is Dongfangshan.

Cultivated plant seedlings have been asexually reproduced and have proved to be stable and uniform and have characteristics distinct from known plants. Seedling plants were found in a cultivated state. Unique characteristics of this new cultivar as herein described are firmly fixed and retain the identical distinguishing characteristics of the new cultivar through successive generations of asexual propagation. This cultivar has use in afforestation, establishing a forest network or a tree coastal shelter belt and for landscaping along rivers, in parks and in communities.

The Descripton Of ×*Taxodiomera peizhongii's* Particularity Relative To Its Parent ×*Taxodiomeria peizhongii* belongs to *Taxodium* of *Taxo diaceae,* which originated from the wide cross of *Taxodium mucronatum* Ten (♀) and *Cryptomeria fortunei* (♂). The main configuration of ×*Taxodiomeria peizhongii* is similar to maternal *Taxodium mucronatum* Ten, the phenomenon of biased maternal inheritance of ×*Taxodiomeria peizhongii* is also approved by RAPD analysis, the analysis makes it clear that the genetic distance (0.210–0.246) between ×*Taxodiomeria peizhongii* and maternal *Taxodium mucronatum* Ten is far less than the genetic distance (0.757–0.764) between it and paternal *Cryptomeria fortunei.* Its main characters are: (1) its base of stem is round and regular without buttress root, close to paternal *Cryptomeria fortunei,* whereas its maternal *Taxodium mucronatum* Ten has buttress root; (2)the bark of *Taxodium mucronatum*Ten cracks into strips, but the ×*Taxodiomeria peizhongii* has transverse cracks besides split cracks and its bark cracks into flakes; (3) there often are several main crotches five to eight meters above ground in the ×*Taxodiomeria peizhongii's* trunk stem, its canopy is nearly elliptic shape, this is obviously differ from its maternal and paternal plant, there is obviously no crotch in the trunk stem of maternal *Taxodium mucronatum* Ten, and the canopy extends to wide conic shape, however the canopy of *Cryptomeria fortunei* is long elliptic shape in common; (4) there are only male conglobate fruit on the adult tree of more than 30 years old, arranging in vertical disposition, see the type specimen (picture 2), and no female conglobate fruit on the adult tree, and it cannot reproduce with sexual propagation manner.

Origin And Asexual Reproduction Of The New Cultivar

*Taxodium mucronatum* Ten belongs to *Taxodium* of Taxodiaceae and is a tall deciduous or semi-indeciduous arbor species, which originated in Mexico and in Texas and was introduced to the Peoples Republic of China in about 1925.

The *Cryptomeria fortunei* is belong to *Cryptomeria D.* Don of taxodiacae, it is evergreen tall arbor, and is originated in Zhejiang Province of China. In 1962, after pollinating *Taxodium mucronatum* Ten at Nanjing, China using pollen of *Cryptomeria fortunei,* we obtained three cones. By seeding them, we were able to produce twelve seedlings. We selected five of them after planting, More than 6,000 seedlings were obtained in 1972 after stem planting.

×*Taxodiomeria peizhongii* has been spread and planted experimentally after thirty years of studies conducted by Shanghai Central Station of Forestry including afforestation, cultivation and propagation tests (asexual reproduction in a cultivated state) under different ecological conditions. Such studies included detailed research on its germplasm characters and its ecological value. Presently there is a ×*Taxodiomeria peizhongii* population of about 2,000 thirty-year-old trees in the Peoples Republic of China with the tree population growing on land having a salt content of 3.9%. Some of that tree population is growing with the base and root system submerged in water, while other trees of that population grow under various ecological areas such as riversides and parks.

Through Genetic Comparing The ×*Taxodiomeria peizhongii* Is Proved To Be A New Steady Breed.

In the whole Chuansha forestry center with more than 1000 trunks ×*Taxodiomeria peizhongii,* its stand forest structure is accordant.

After three continuous years observation on-site and collecting in the collecting sites of Songjiang Drunk-white Pool, Xinqiao Nursery, Jinshan Shore Park, the plant area of Petrochemical Complex, the double bank of Chuanyang River in Pudong New Area, Yangjing Nursery, Chuansha Forestry Centre and other sites of Najing and Zhenjiang, it is shown that there is no difference in the configuration between different sites.

In recent years, the materials gathered from the collecting sites of Songjiang Drunk-white Pool, Xinqiao Nursery, Jinshan Shore Park, the plant area of Petrochemical Complex, the double bank of Chuanyang River in Pudong New Area, Yangjing Nursery, Chuansha Forestry Centre and other sites of Najing and Zhenjiang are accordant, all no female conglobate fruit, there is no different instance relative to type specimen The stem structures, branch characters and canopy shapes are all comparatively accordant.

The Detailed Examples Of Asexual Propagation Of ×*Taxodiomera peizhongii*

We researched the approach of asexual propagation of ×*Taxodiomeria peizhongii,* the specific methods are as follows: hardwood cutting, greenwood cutting, tissue culture, graft and etc., it is proved through practicing that greenwood cutting and graft are the better methods. Our primary location for asexually reproducing ×*Taxodiomeria peizhongii* is the Chuansha forest farm of Pudongdistrict, No. 888, Jiuxin Road, JiutingTown, Shanghai.

Greenwood cutting

Use the current growth half-lignified shoot of ×*Taxodiomeria peizhongii* to be the cutting wood, cutting in the seasons of early summer (plum season), midsummer and early autumn, furthermore, can cut in the winter utilizing the establishment of greenhouse. Among them, the effects of cutting in plum season and winter are the best, the rooting rate can reach 72%–75%, higher than the rooting rate of cutting in midsummer and early autumn.

Specific method

Cut the shoot into a cutting wood of 10~12 cm with a sharp knife, the notch must be smooth. Before cut, the cutting wood should be dipped rapidly into naphthyl acetic acid of 500 ppm or dipped in naphthylacetic acid of 50 ppm for 6 hours, the cutting wood must be cut in medium(coarse yellow sand, plant ash, pearl sand or roseite) by ⅔ or ½. After cutting, compress tightly the medium, water completely and do the treatment of shading and wetting, it can root after 40~60 days well managing like this.

Grafting

Graft in early spring before foliation.

Use the seedling of annual *Taxodium ascendens Brongn* or *Taxodium distichum* as tree stock, take the vigorous annual shoot without diseases and insect pests as scion wood, and trim the scion wood to be a scion with only 2–3 buds, adopt the method of "heart center approach grafting", when the graft is surviving, do the stock tip pruning, but remain a preponderant bud on the scion wood, and well foster it, therewith its growth can be more than 1M.

SUMMARY OF THE INVENTION

Distinctive characteristics of ×*Taxodiomeria peizhongii* include: (1) its base of stem is round and regular without buttress root; (2) its bark cracks into flakes (3) there are several main crotches five to eight meters above ground, (4) its canopy is nearly elliptic shape; (5) there are only male conglobate flower and no female conglobate fruit on the adult tree, and (6) it only reproduces asexually. ×*Taxodiomeria peizhongii* also possesses additional good properties including saline tolerance (salt content is below 3.9%), alkali tolerance (7≦pH ≦8.9), moisture resistance and provides good landscape effect. ×*Taxodiomera peizhongii* is suitable for afforestation and establishing farmland, forest network, and coastal shelter belt on intertidal zones. ×*Taxodiomeria peizhongii* grows well in alkali soils, alkaline lands, marsh, riverbanks, gardens, spark landscapes, factories and communities.

×*Taxodiomera peizhongii* has been successfully exactly reproduced from its originating as a seedling using asexual reproduction methods such as twig cuttage, a asexual reproduction produces an exact copy of the ×*Taxodiomeria peizhongii* plant which is identical to the original plant in every distinguishing characteristic.

BRIEF DESCRIPTION OF THE PHOTOGRAPHS

FIG. 1 shows the biggest ×*Taxodiomeria peizhongii* tree, a thirty-year-old tree growing in Chuansha Forestry Center, Shanghai, Peoples Republic of China. Its diameter at breast height is 62.5 cm. Its stem requires two persons to fully clasp hands to reach around the perimeter of the tree.

Figure 1:
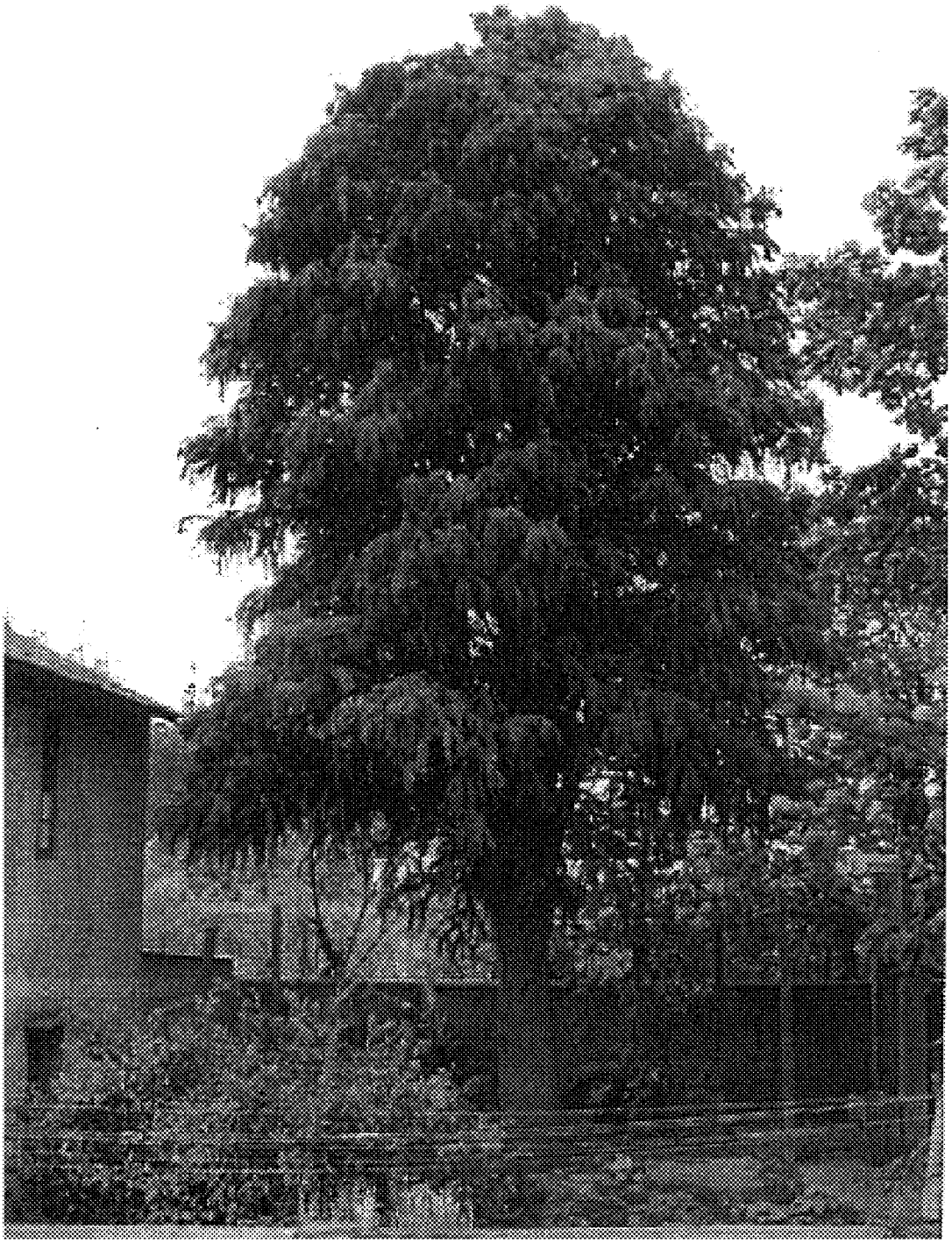
Figure 2:
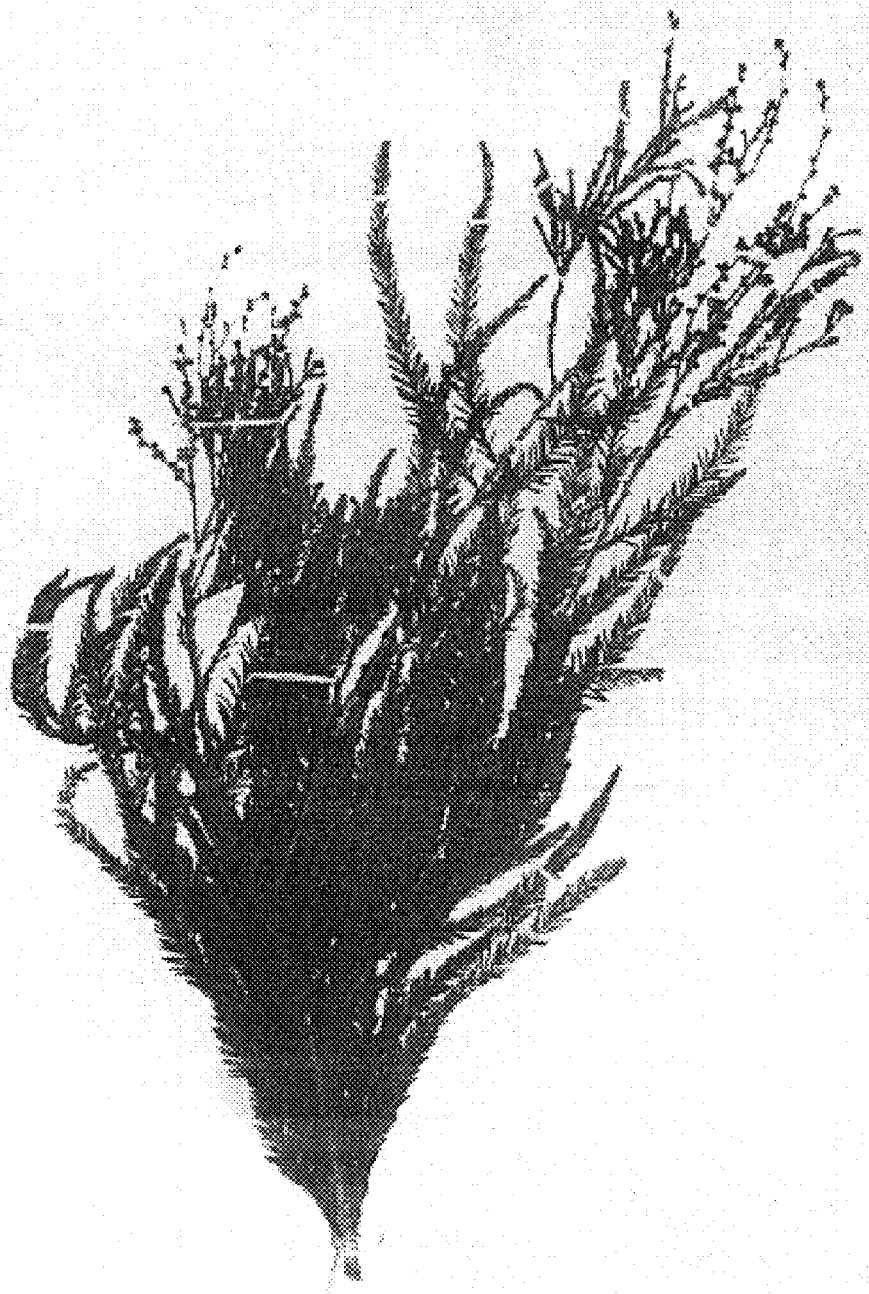
FIG. 2 shows a branch of ×*Taxodiomeria peizhongii.*
Figure 3:
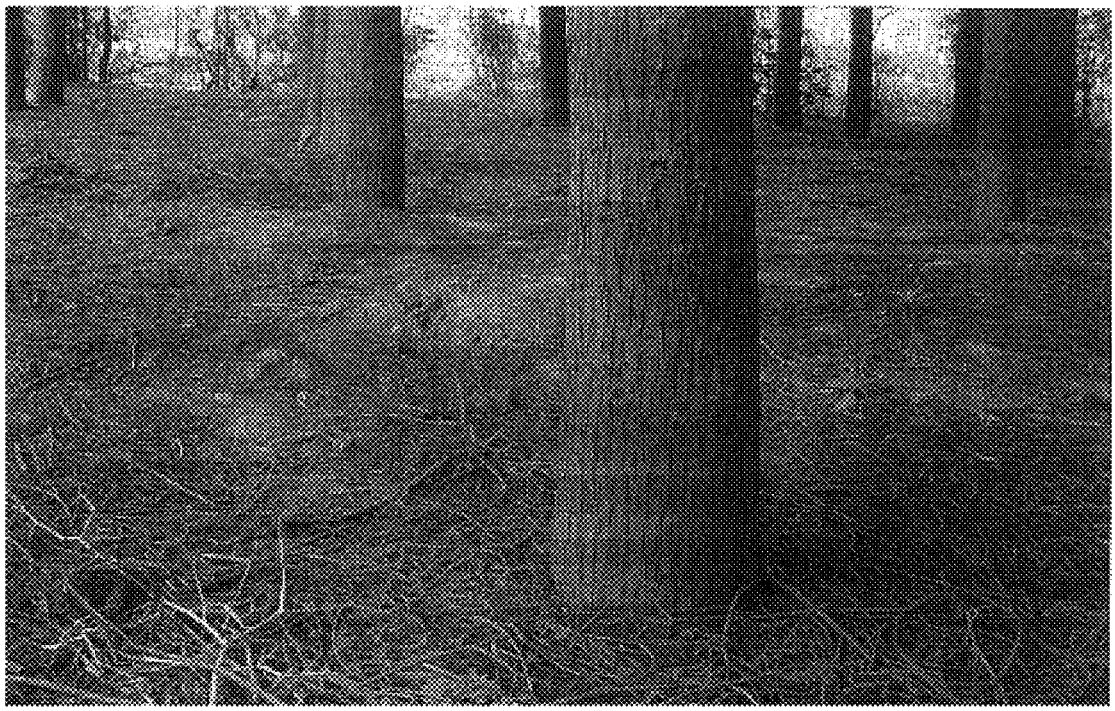
FIG. 3 shows one of the characteristics of ×*Taxodiomeria peizhongii;* round and regular stem base. The stem base of ×*Taxodiomeria peizhongii* is round and regular without buttress roots.
Figure 4:
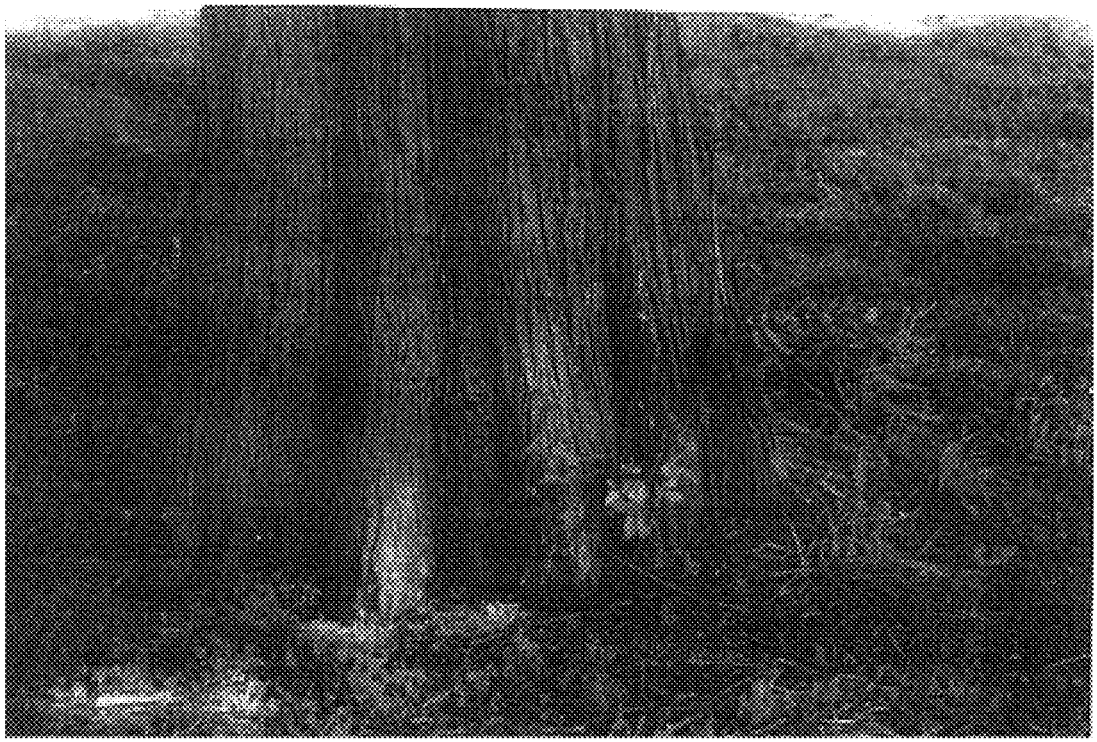
FIG. 4 shows *Taxodium mucronatum* Ten, the control variety of ×*Taxodiomeria peizhongii,* which has distinct buttress roots.
Figure 5:
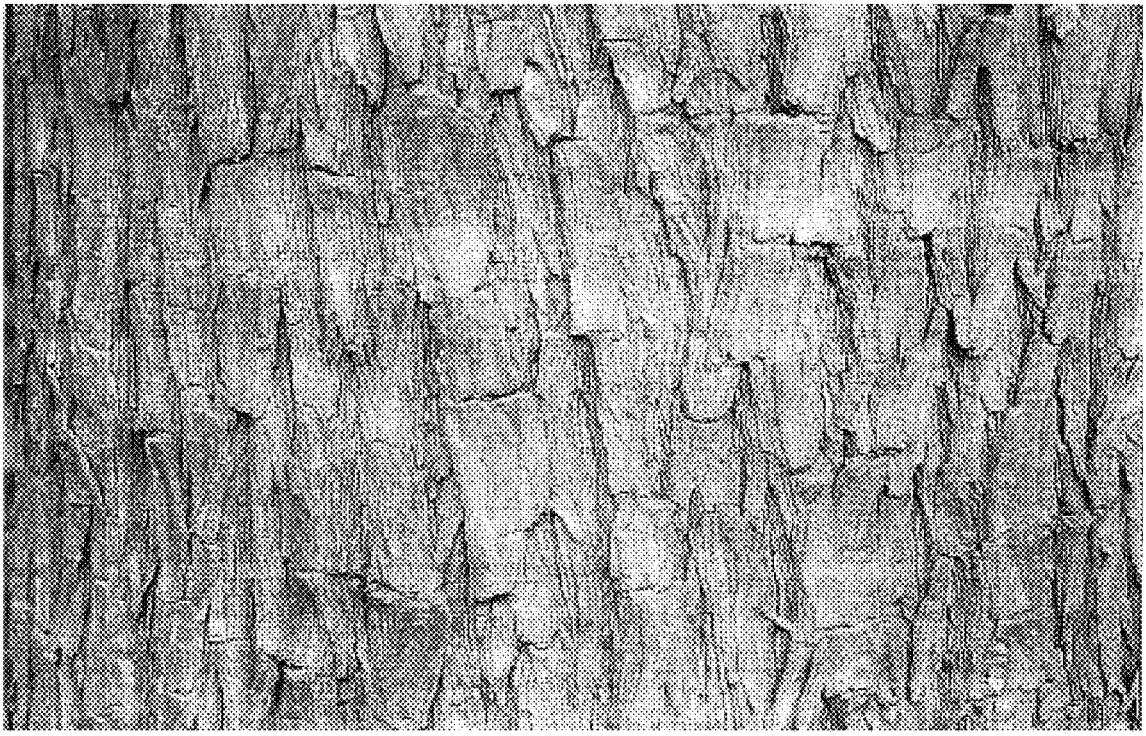
FIG. 5 shows a second characteristic of ×*Taxodiomeria peizhongii;* its flaky bark.
Figure 6:
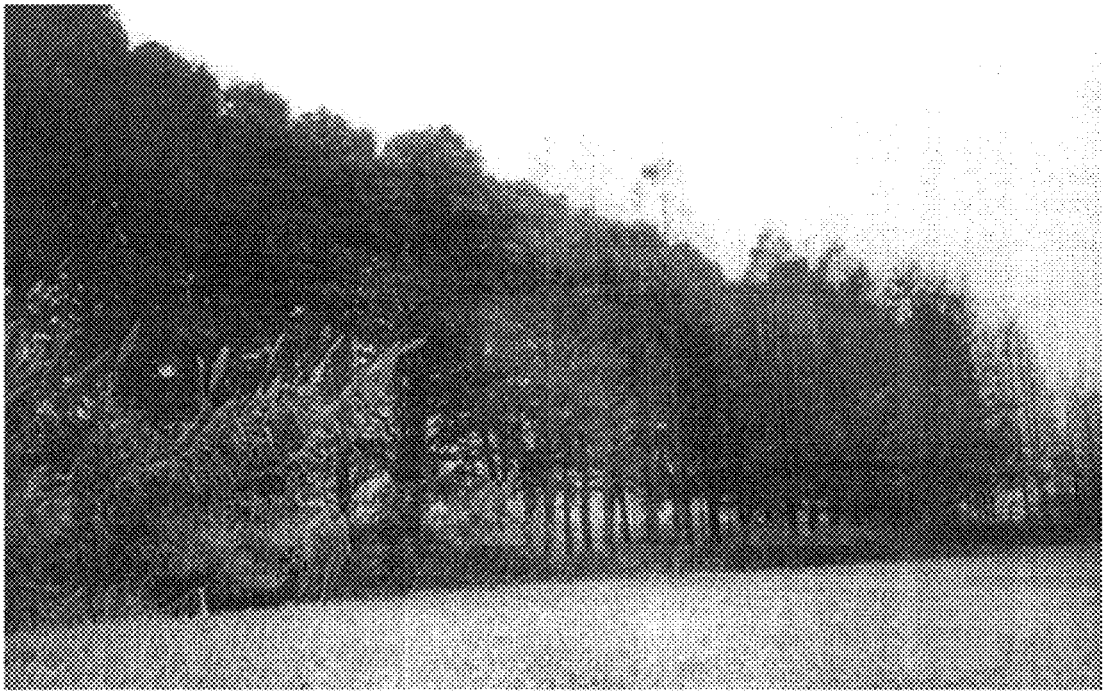
FIG. 6 shows a semi-indeciduous characteristic of ×*Taxodiomeria peizhongii.*—×*Taxodiomeria peizhongii* is lush and its foliage begins to fall off at the end of the calendar month December, while the foliage of metasequoia falls off after November.
Figure 7:
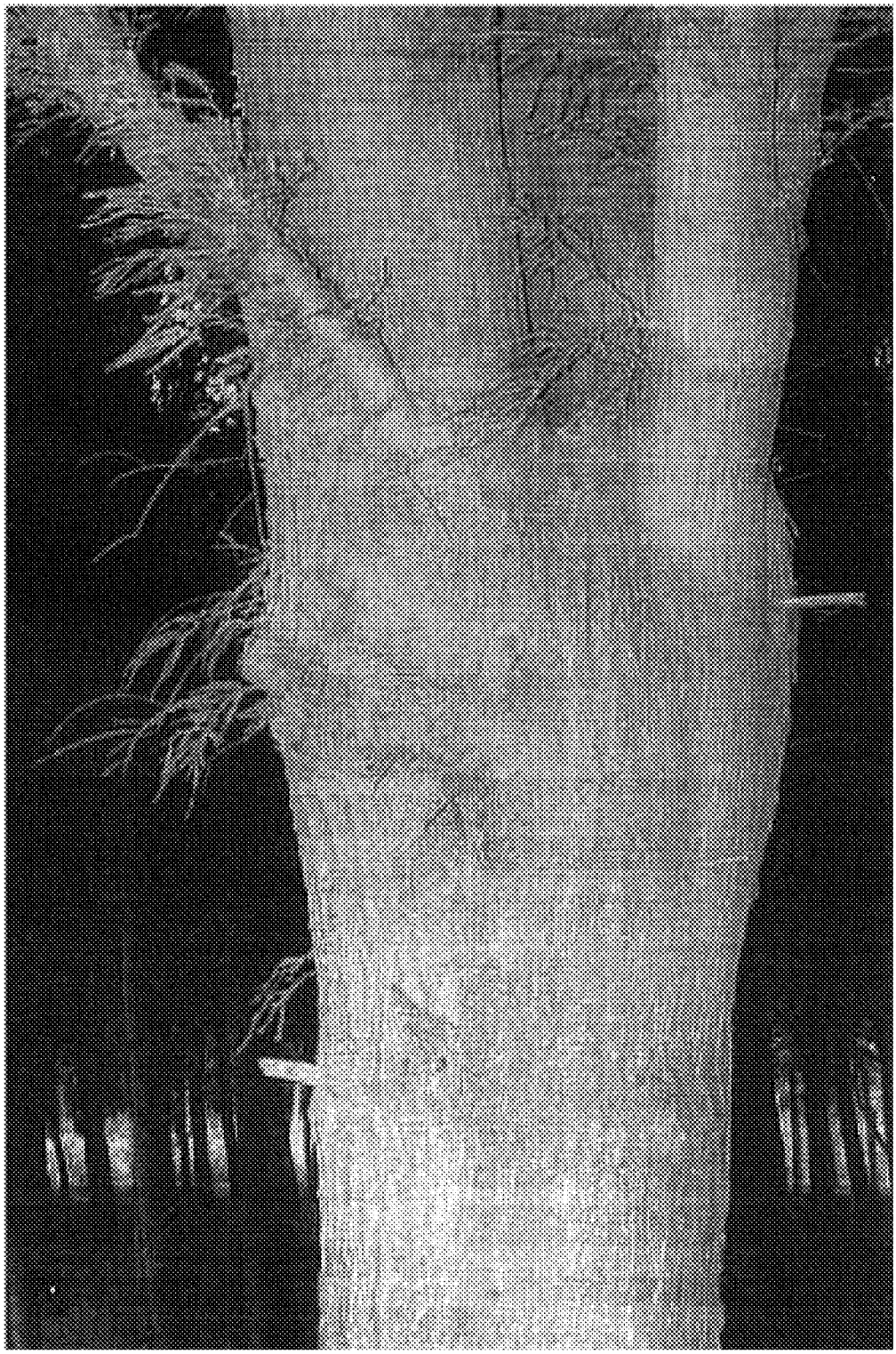
FIG. 7 shows a third characteristic of ×*Taxodiomeria peizhongii;* multiple crotches on the trunk. There are always several crotches on the trunk five to eight meters above ground.
Figure 8:
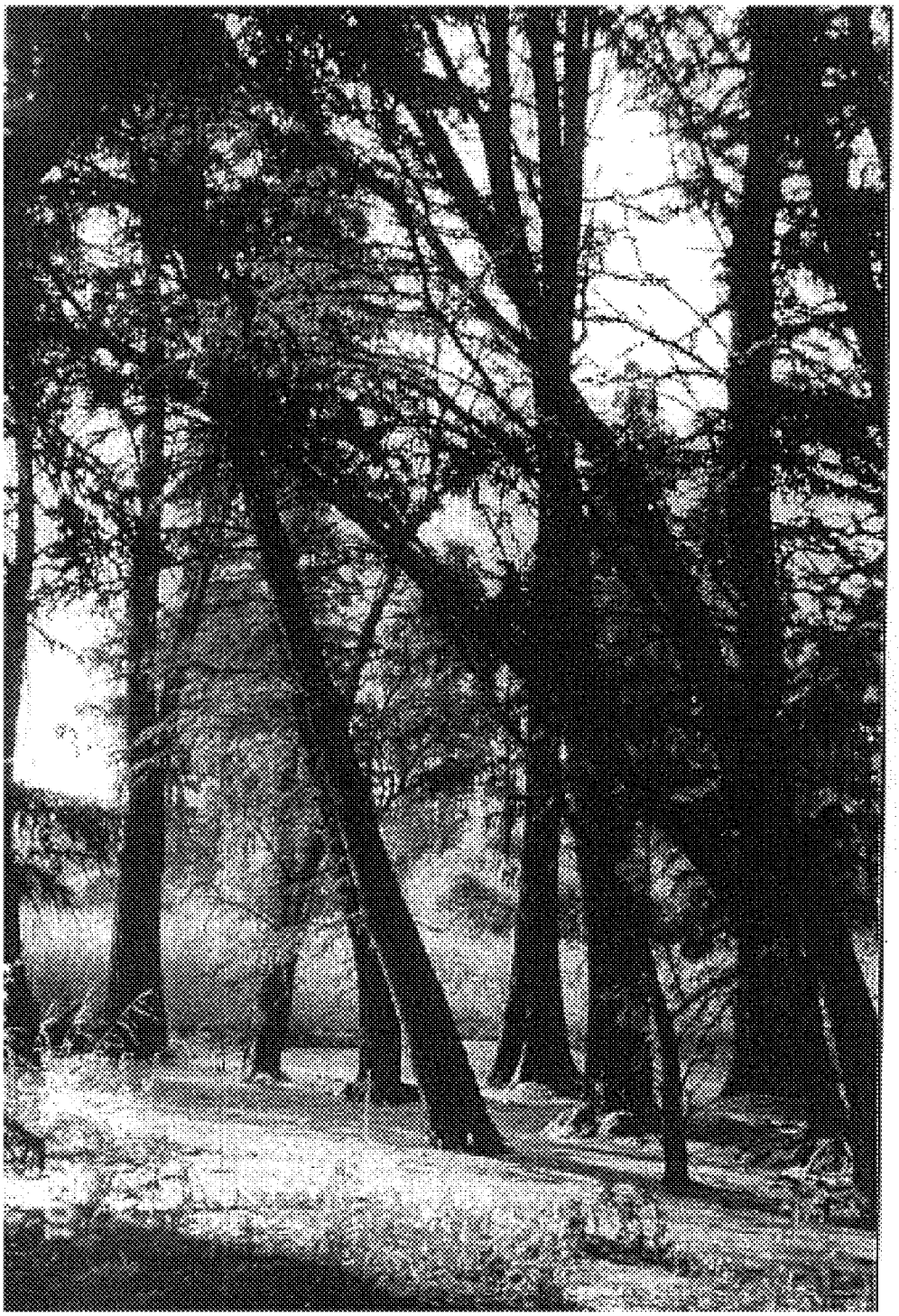

FIG. 8 shows the moisture tolerance characteristic of ×*Taxodiomeria peizhongii*. In Songjiang Xinqiao Xinjie Nursery of Shanghai city, several scores of ×*Taxodiomeria peizhongii* have grown for almost twenty years in the river due to the collapse of some of the riverbank which occurred in the 1980's. The growth vigor of these trees growing in the river is comparable to those trees which remained growing on a remaining part of the riverbank.

Figure 9:
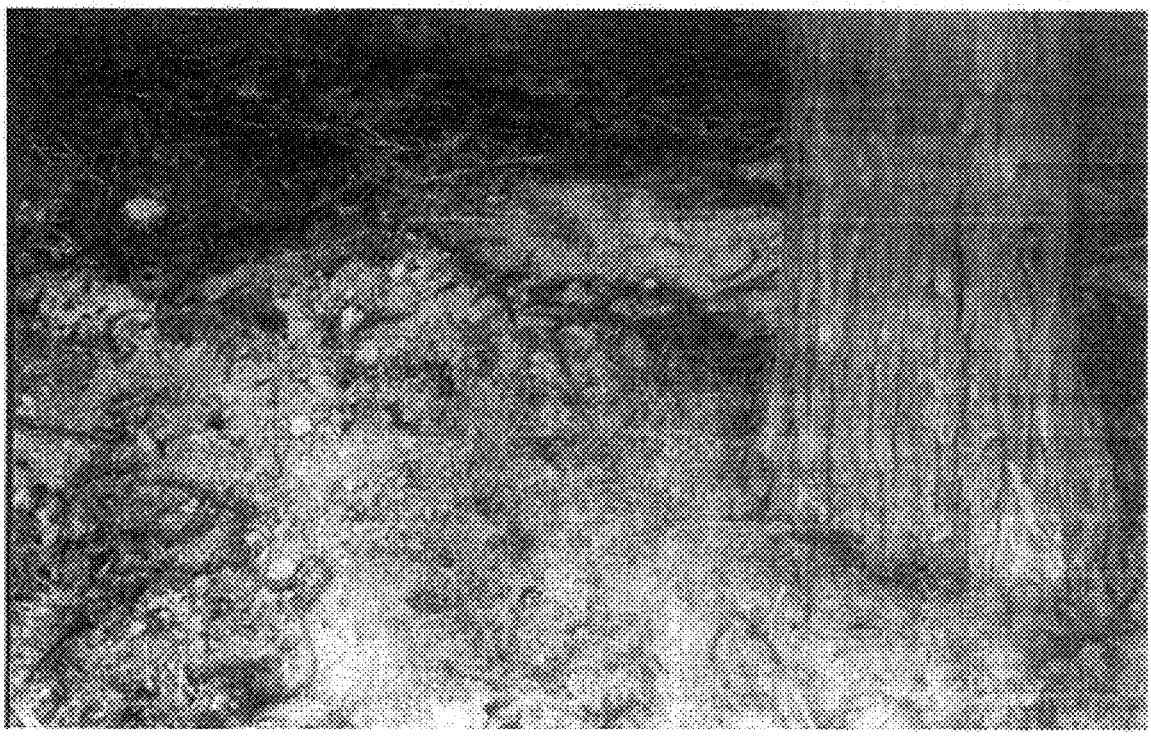

FIG. 9 shows saline and alkali tolerance characteristics of ×*Taxodiomeria peizhongii*. Jinshan Binhai Park in Shanghai city is reclaimed beach land. Even though salt concentration of this sloping forest land reaches 3.9%, ×*Taxodiomeria peizhongii* still grows.

Figure 10:
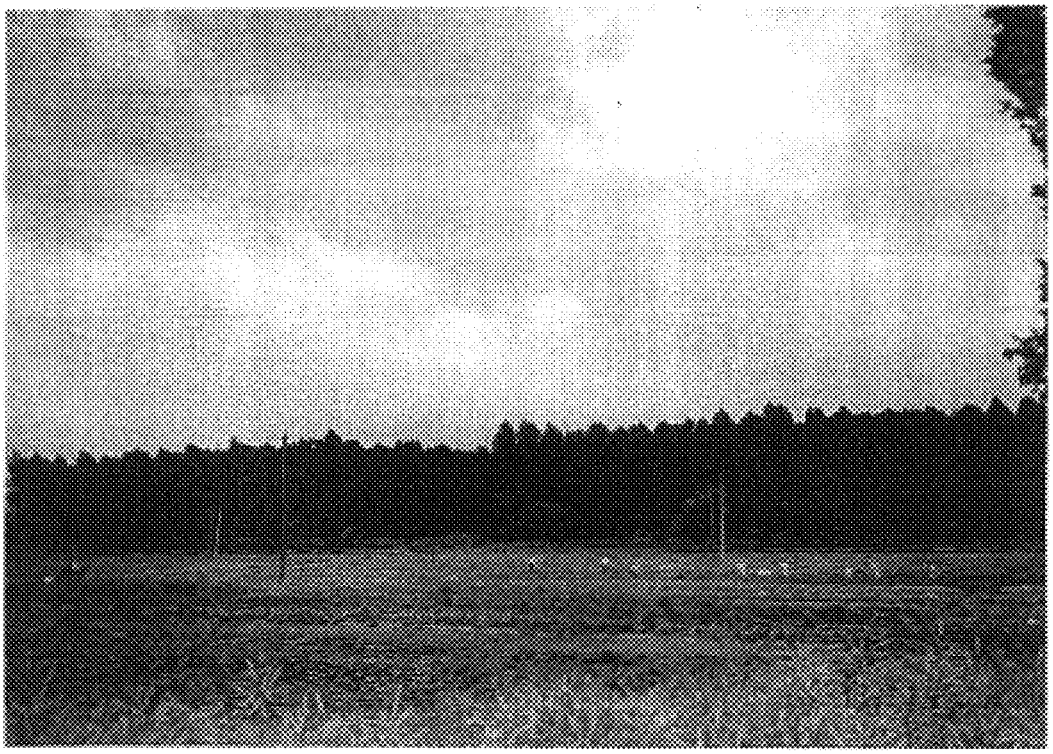

FIG. 10 shows a landscape view of the biggest ×*Taxodiomeria peizhongii* forest in China ×*Taxodiomeria peizhongii* forest in Chuansha Forestry Center. Chuansha Forestry Center is located on one of the main pathways of typhoon(s) from the sea to Shanghai city. The pH value of the forestry center soil is about 8.6. However, ×*Taxodiomeria peizhongii* grows very well in this alkali soil.

Figure 11:
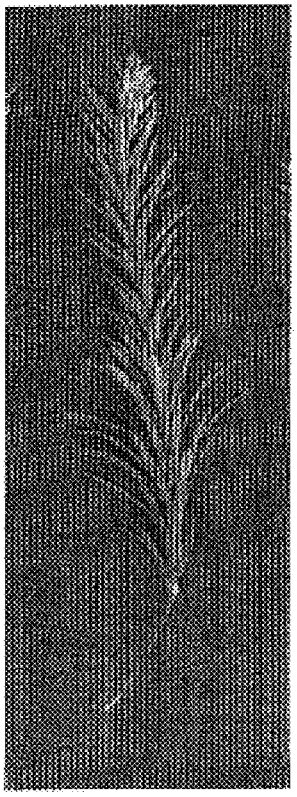

FIG. 11 shows needle leaves of the ×*Taxodiomeria peizhongii* arranged in a feather pattern at two years old.

Figure 12:
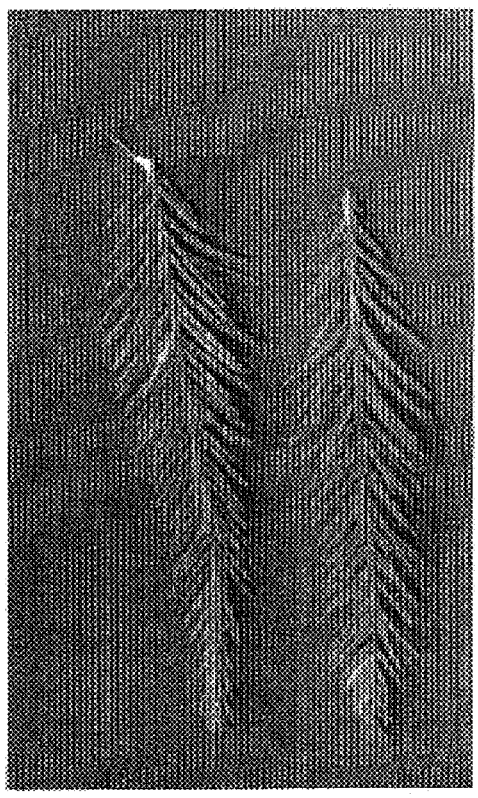

FIG. 12 shows needle leaves of the ×*Taxodiomeria peizhongii* at two years old.

Figure 13:
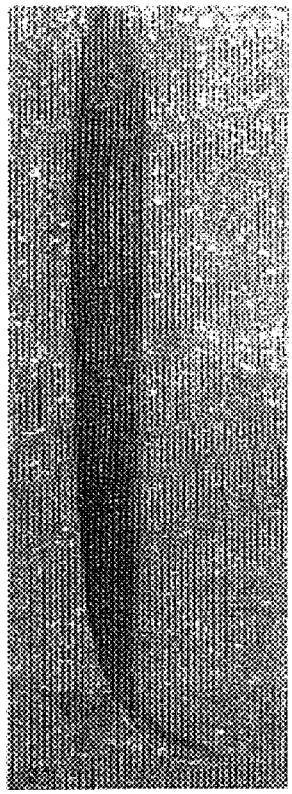

FIG. 13 shows a stomatal band of the ×*Taxodiomeria peizhongii* on the leaf surface.

Figure 14:
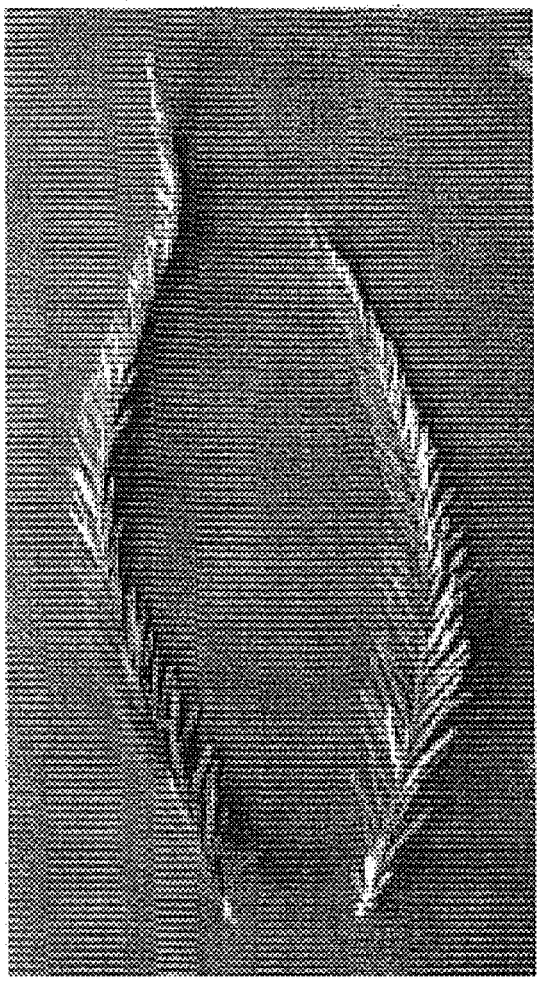

FIG. 14 shows needles leaves of the *Taxodium mucronatum*×*Cryptomeria fortunei* (filial generation) at the age of 28.

Figure 15:
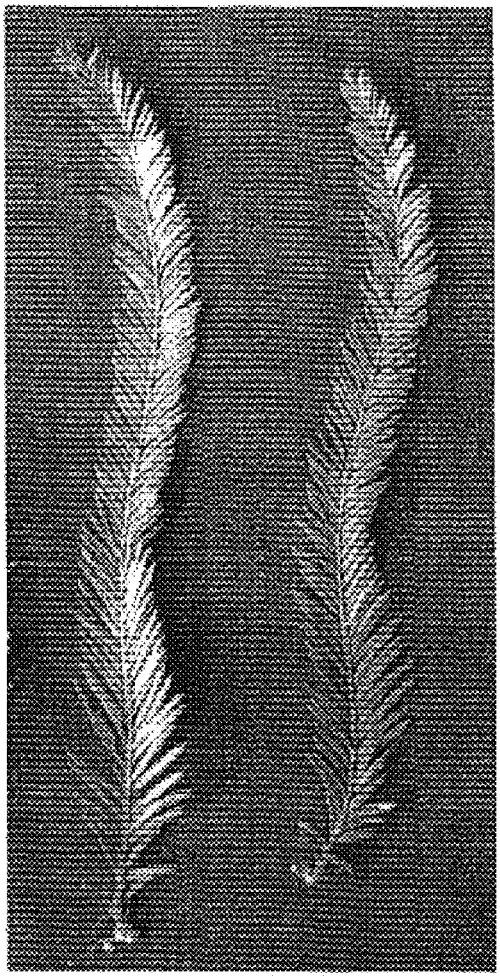

FIG. 15 shows needle leaves of the *Taxodium mucronatum* Tenore (maternal plant) at the age of 80.

Figure 16:
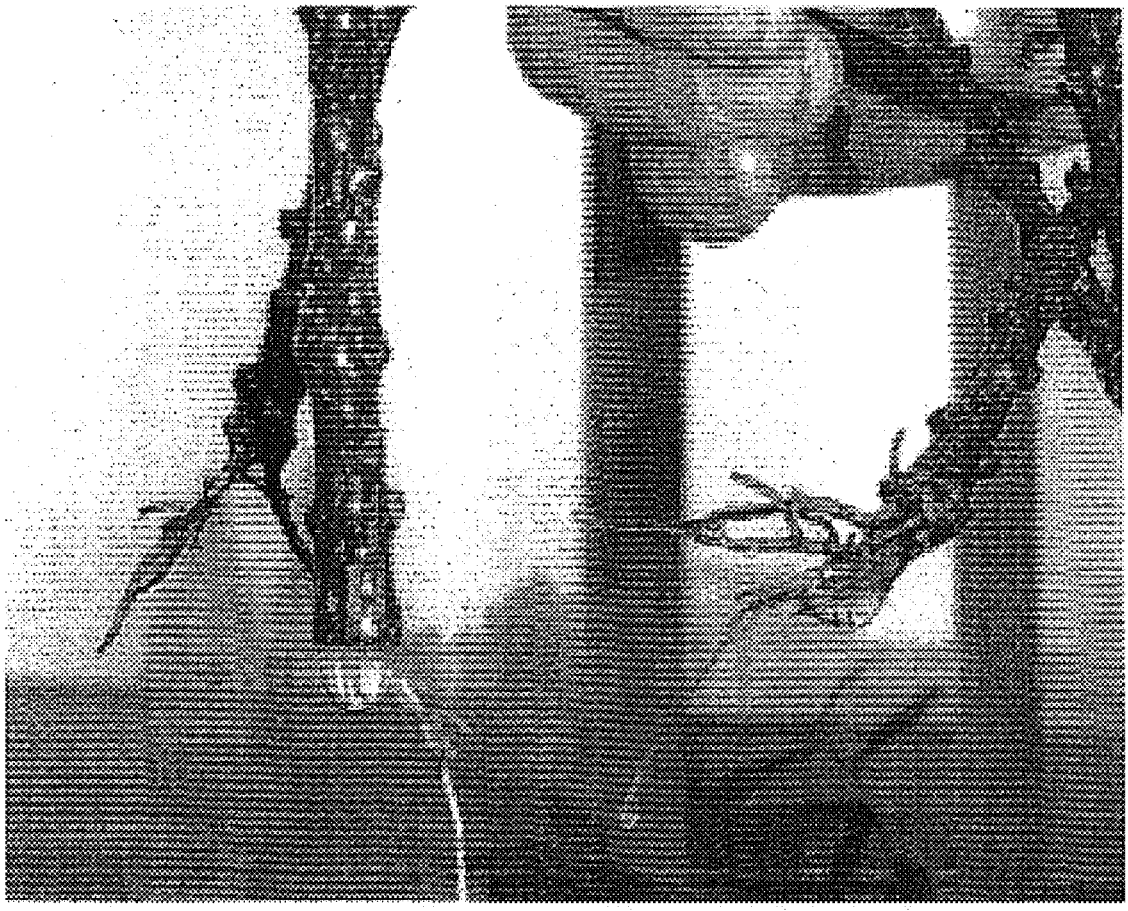

FIG. 16 shows the *Taxodium mucronatum*×*Cryptomeria fortunei* cuttage in water and rooting.

Figure 17:
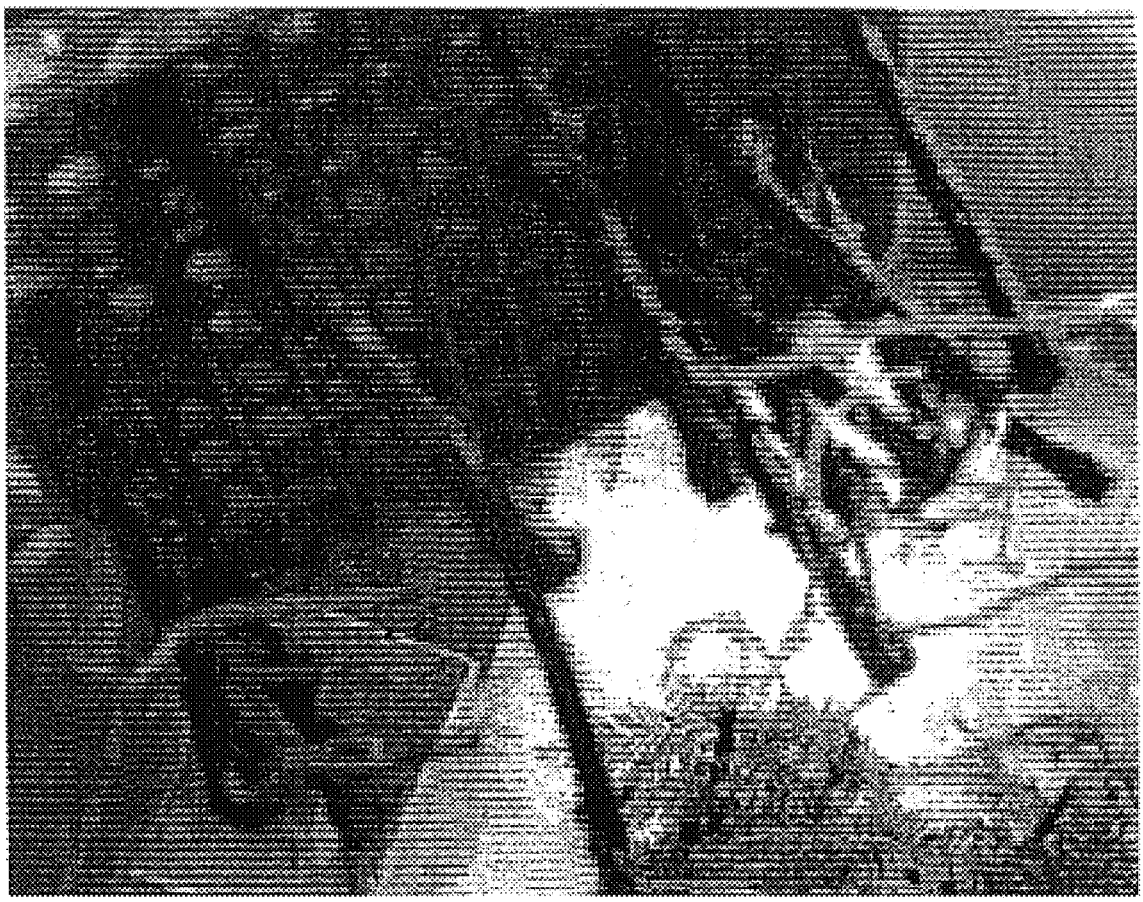

FIG. 17 shows the *Taxodium mucronatum* Tenore cuttage in water and rooting.

BOTANICAL DESCRIPTION OF THE PLANT

The main botanical characteristics of ×*Taxodiomeria peizhongii* follows:

Plant:

*Latin name:* ×*Taxodiomeria peizhongii.*
*Cultivar name.*—'Dongfangshan'.
*Plant height.*—18 meters/30 year old tree.
*Canopy.*—Columnar coniform.
*Florescence.*—Month of April.
*Optimal temperature.*—15° C.–30° C.
*Seed and fruit productivity.*—About 40-year-old trees have not been found to fruit.
*Characteristics.*—Tall indeciduous or semi-indeciduous arbor species.
*Habits.*×*Taxodiomeria peizhongii* likes light, warm and humid climate, and wet soil; endures half-shade, moisture, salt alkali and impoverishment and resists wind well.

Stem or trunk and branch:

*Base.*—Round and regular.
*Diameter breast height.*—55–62.5 cm for 40-year-old tree.
*Tapering grade.*—Small.
*Ramification characteristic.*—There are crotches on the trunk.
*Bark color.*—Taupe.
*Bark crack.*—Be strip and broadways cracks into flakiness.
*Lateral branches.*—Stretch horizontally or upwards aslant.
*Persistent twigs.*—Grayish or henna and slippery, and with 1–1.5 mm diameter.
*Fallen twigs.*—Green.
*Distance among branches.*—Sparse.
*Twigs on big tree.*—Slender.

Foliage.

*Shape.*—Strip filate.
*Length.*—3–10 mm.
*Width.*—0.8–1 mm.
*Arrangement.*—Foliages on pleurogenous twigs array in two parallel rows, and the persistent twigs array parallel.
*Color.*—Dark greenish-black color.
*Stalk and basal.*—Short stalk and decurrent basal.
*Angle with the stem.*—30 degree with pinnate foliage and 10–15 degree with twisted foliage.
*Venation.*—Midrib is greenish black.
*Thickness.*—0.2–0.3 mm.

The leaf is needle strip and holophyllus. There is one stomatal band on each side of the midrib of the leaf face, and the breadth is about half of the leaf; there is no stomatal band on the back of the leaf.

Fruit:

*Insertion manner of staminate flower.*—The 2.5–3 mm round staminate flowers persist on the two of twigs.
*Female cone.*—No female cone has been found.

The "average plant spread" for various ages is as follows: 0.55 $m^2$ at age two; 0.98 $m^2$ at age three; 1.58 $m^2$ at age four; 2.65 $m^2$ at age five; and 54.86 $m^2$ at age twenty-eight.

This is a brand-new plant variety with adaptability characteristics that can grow well in all kinds of ecological conditions.

The plant claimed is ×*Taxodiomeria peizhongii.*

The main botanical characteristics of the female parent of ×*Taxodiomeria peizhongii* follow:

Plant:

*Latin name.*—*Taxodium mucronatum Ten.*
*Generic name.*—*Taxodium.*
*Specific name.*—*Taxodium mucronutun.*
*Plant height.*—50 meters in its native habitat.
*Canopy.*—Wide coniform.
*Florescence.*—Month of April.
*Optimal temperature.*—15° C.–30° C.
*Seed and fruit productivity.*—This new variety can bear fruit in its native habitat, and cannot fruit without having completed its blooming period.
*Characteristics.*—Tall indeciduous or semi-indeciduous arbor species.
*Habits.*—It likes light, warm and humid climate and wet soil. It has good endurance to moisture and resists wind.

Stem or trunk and branch:

*Base.*—There are buttress roots on its base.
*Diameter breast height.*—Four meters in its native habitat.

*Tapering grade.*—Great.
*Ramification characteristic.*—There are always crotches on its trunk.
*Bark color.*—Ficelle.
*Bark crack.*—Flaky strip.
*Lateral branches.*—Stretch upward aslant or horizontally.
*Persistent twigs.*—Dark taupe and slippery, and with 1.5–2 mm diameter.
*Fallen twigs.*—Green.
*Distance among branches.*—Moderate.
*Twigs on big tree.*—Slender.
*Shape.*—Strip filate.
*Length.*—3–15 mm.
*Width.*—1 mm.

Foliage:
*Arrangement.*—Foliages on pleurogenous twigs array in two parallel rows, and persistent twigs array parallel.
*Color.*—Bottle-green.
*Stalk and basal.*—Short stalk and decurrent basal.
*Angle with the stem.*—30 degree for the pinnate foliages and 10–15 degree for the helical foliages.
*Venation.*—Midrib is greenish black.
*Thickness.*—0.2–0.3 mm.

Fruit:
*Insertion manner of staminate flower.*—2.5 mm–3 mm round staminate flowers persist on the top of twigs.
*Female cone.*—Solitary female cones persist on the top of twigs.
*Fruit stalk.*—There is almost no stalk.
*Shape.*—It is obovate round, and there are seminiferous scale enations on it.
*Color.*—Green to chocolate brown.
*Size.*—15 mm–25 mm diameter.
*Maturation stage.*—Months of October to November.
*Seminiferous scale.*—Ligneous and scutellate, two seeds on its ventral side.

Seed:
*Shape.*—Irregular triangle, and has obvious ridges.
*Color.*—Dark fulvous.
*Length.*—4 mm–5 mm.

The main botanical characteristics of the male parent of ×*Taxodiomeria peizhongii* follow:

Plant:
*Generic name.*—*Cryptomeria D. Don.*
*Specific name.*—*Cryptomeria fortunei.*
*Plant height.*—About 40 meters in its native habitat.
*Canopy.*—Columnar coniform.
*Florescence.*—Month of April.
*Optimal temperature.*—14° C.–25° C.
*Seed and fruit productivity.*—It can fruit.
*Characteristics.*—Tall indeciduous arbor species.
*Habits.*—It likes light, humid cool climate and loose soil with good drainability; and it endures half-shade and impoverishment.

Stem or trunk and branch:
*Base.*—Round and regular.
*Diameter breast height.*—About 3 to 4 meters in its native habitat.
*Tapering grade.*—Small.
*Ramification characteristic.*—Erect trunk Bark color: taupe.
*Bark crack.*—Long strip flakiness.
*Lateral branches.*—Stretch horizontally or bend downwards.
*Persistent twigs.*—Reddish brown, have grooves under foliages and the diameter is about 2 mm–4 mm.
*Distance among branches.*—Moderate.
*Twigs on big tree.*—Thicker.

Foliage:
*Shape.*—Conical top end, and bend inwards.
*Length.*—5 mm–15 mm.
*Width.*—0.5 mm–1 mm.
*Arrangement.*—Foliages array in five rows helically.
*Color.*—Emerald.
*Stalk and basal.*—Short stalk and decurrent basal.
*Angle with the stem.*—15 degree 30 degree.
*Venation.*—Midrib is not obvious, and there are pore lines around the midrib.
*Thickness.*—0.8–1 mm.

Fruit:
*Insertion manner of staminate flower.*—5–6 mm elliptical flowers persist on the top axillae of twigs.
*Female cone.*—Solitary female cone on top of twig or fasciculate cones.
*Fruit stalk.*—There is almost no stalk.
*Shape.*—It is near round with triangular enations on it.
*Color.*—Green to chocolate brown.
*Size.*—Diameter 12 mm–20 mm.
*Maturation stage.*—Month of October.

Seed:
*Seminiferous scale.*—Ligneous and scutellate, and two seeds in it.
*Shape.*—Irregular triangle, and with narrow wing.
*Color.*—Puce.
*Length.*—4 mm–5 mm, width: 2 mm–3 mm.

Morphological description: Semi-evergreen arbor, the tapering degree of the trunk is smaller than that of *T. mucronatum* Tenore. The bark is cracked into strips. There are two attachment types for needle leaves, one attachment type includes needle leaves of separated branches arranged with a type of feather in two rows in the pattern of a broad V type (FIG. 11), and the torsional part of the leaf base is not smooth (while the torsional part of the leaf base is smooth for *T. mucronatum* Tenore). The second attachment type includes needle leaves of separated branches grown in the spiral type (FIG. 12). There are two stomatal bands separately distributed over the two sides of a median vein on the surfaces of need leaves, which width is about ½ of the leaf width (FIG. 13), and there is no stomatal band on the back of leaves. Needle leaves on the lower part of separated branches are obviously longer than those on the upper part, and the whole separated branches are in the shape of tails and tips (FIG. 14), while for *T. mucronatum* Tenore, as its maternal plant, the needle leaves on the anterior part are of the same length, with no shape of tails or tips (FIG. 15).

Color description:

Described samples are from the forestry centre of Chuansha City on Sep. 16, 2005. The colors are described according to a R.H.S. Color Chart as follows:
*Pollen cone.*—G138A.
*Cone.*—GO173B.
*One-year shoots.*—GO174B.
*Two-year shoots.*—GG197A.
*Leaf surface.*—GG137A.
*Leaf back.*—GG137C.
*Bark.*—GO177B.

Site of Asexual Reproduction and More Detailed Distributive Information for *T. mucronatum*×*C. fortunei*

Rooting situation: The rooting form of the cuttage and reproduction for the tender branches of *T. mucronatum*×*C. fortunei* (the turves and perlites are used as the matrix) (both callus rooting and cortex rooting exist); cuttage in water is used for the callus rooting (FIG. 16), while for *T. mucronatum* Tenore, cortex rooting is the main pattern (FIG. 17).

Distributive situation: Shanghai City, Nanjing City of Jiangsu Province, Shaxi Town of Taicang City, Jiangsu Province, Wuhan City of Hubei Province.

TABLE 1

Trial Cultivation of *T. mucronatum* × *C. fortunei*

| Loc. | Lat. and Long. | Average Annual Rainfall | Temp. (° C.) | Average Annual Temp. | Soil Type |
|---|---|---|---|---|---|
| Shandong | 36° 28' N 117° 20' E | 710 mm | −22.5–41 | 12.9 | Medium loam |
| Henan | 34° 55' N 113° 22' E | 550 mm | −18.9–44.1 | 14.4 | Loamy moisture soil |
| Hunan | 28° 36' N 111° 42' E | 1750 mm | −5–40.5 | 17.3 | Sandy soil |
| Jiangxi | 28° 44' N 115° 45' E | 1713 mm | −8.9–38.6 | 17.3 | Red loam |
| Guangxi | 22° 52' N 108° 22' E | 1300 mm | −2–39.4 | 20.5 | Red loam |

| Loc. | Soil PH Value | Pond time | Plant Date | Survival percent. | Annual Height incr. | Growth Potential |
|---|---|---|---|---|---|---|
| Shandong | 7.0 | 3 days | Mar. 19, 2005 | 64% | 69 cm | Good |
| Henan | 8.2 | | Mar. 13, 2004 | 4% | 30 cm | Good |
| Hunan | 7.5 | 15 days | Feb. 18, 2004 | 67% | 180 cm | Good |
| Jiangxi | 5.5 | | Mar. 25, 2005 | 82% | 24 cm | Medium |
| Guangxi | 5.5 | | Apr. 10, 2005 | 86% | 32 cm | Medium |

According to the observation, there is a large difference in the growth for annual cuttage cultivation in different districts. Growth will be prevented when planted in an alkaline soil, and aetiolation also may occur, with weak growth potential. The average height and diameter will be respectively 0.5 m and 0.8 cm after one year since being cultivated. However, in the non-saline-alkali soils, it grows rapidly, with no aetiolation, and the average height and diameter will be respectively 0.8 m and 1.2 cm after one year since being cultivated. It indicates that *T. mucronatum*×*C. fortunei* has limited resistance to the alkaline and saline, and cultivation of high quality forest seedlings should be finished in the soils of medium fertility.

According to the results of the preliminary cultivation experiments in the external provinces and cities, the seedling of *T. mucronatum*×*C. fortunei* is waterproof after rooting, and moreover, it grows more vigorously in the moisture places. In 2004, experiments were done in Changde City of Hunan, continuous ponding was implemented for 15 days in July, and within 3 days of which, seedlings were totally immersed, but the survival percentage reaches 65%, and in that year, its average height increment was 60 cm.

Ecological features: According to the preliminary experiments on the *T. mucronatum*×*C. fortunei* trees distributed over Wuhan and Henan, this hybrid has a broad applicable scope for highest and lowest temperature. In the 1970s, Wuhan City introduced *T. mucronatum*×*C. fortunei,* and up to now, 220 plants are remained. In the past 30 years, Wuhan has encountered the highest temperature of 40° C., the summer drought with the duration of 30–40 days, and the lowest temperatures of −18° C. However, the *T. mucronatum*×*C. fortunei* trees have not been hurt. The average diameter of the trunk is 30–40 cm, and the average height is 22 m, with good growth. Experiments finished in Henan in 2004 showed that *T. mucronatum*×*C. fortunei* can survive under the temperatures between −18.9° C. and 44.1° C.

What is claimed is:

1. A new and distinct variety of ×*Taxodiomeria peizhongii* tree named 'Dongfagshan' as illustrated and described herein.

* * * * *